United States Patent [19]

Radovan et al.

[11] 4,217,889
[45] Aug. 19, 1980

[54] FLAP DEVELOPMENT DEVICE AND METHOD OF PROGRESSIVELY INCREASING SKIN AREA

[75] Inventors: Chedomir Radovan, Woodland Hills; Rudolf R. Schulte, Goleta, both of Calif.

[73] Assignee: Heyer-Schulte Corporation, Goleta, Calif. ; a part interest

[21] Appl. No.: 926,484

[22] Filed: Jul. 20, 1978

Related U.S. Application Data

[63] Continuation of Ser. No. 723,338, Sep. 15, 1976, abandoned.

[51] Int. Cl.² ............................................. A61B 19/00
[52] U.S. Cl. ............................................ 128/1 R; 3/1; 3/1.2
[58] Field of Search .......... 128/1 R, DIG. 25, 350 V, 128/346; 3/1, 1.2, 36

[56] References Cited

U.S. PATENT DOCUMENTS

| | | | |
|---|---|---|---|
| 3,538,917 | 11/1970 | Selker | 128/DIG. 25 |
| 3,665,520 | 5/1972 | Perras et al. | 3/36 |
| 3,744,063 | 7/1973 | McWhorter et al. | 3/1 |
| 3,831,583 | 8/1974 | Edmunds, Jr. et al. | 3/1 X |
| 3,852,833 | 12/1974 | Koneke et al. | 3/36 |
| 3,863,622 | 2/1975 | Buuck | 3/1 X |
| 3,934,274 | 1/1976 | Hartley, Jr. | 3/36 |

OTHER PUBLICATIONS

"The Expansion of an Area of Skin by Progressive Distension of a Subcutaneous Balloon," by Charle G. Neumann, Plastic and Reconstructive Surgery, vol. 19, No. 1, Feb. 1957, pp. 124-130.

Primary Examiner—Ronald L. Frinks
Attorney, Agent, or Firm—Larry N. Barger

[57] ABSTRACT

An expansion device for temporary implantation beneath the skin and subcutaneous layer, there to be enlarged whereby to increase the surface area of tissue which overlays it, to provide a flap for use in plastic and reconstructive surgery. The device comprises an envelope with a substantially non-extensible base and a cover. Together the base and cover form an envelope. The cover is flexible, and when empty it is slack. The volume of the envelope is adjustably variable as a function of the amount of fluid it contains. Means is provided for admitting fluid to the envelope without puncturing the base or the cover.

31 Claims, 13 Drawing Figures

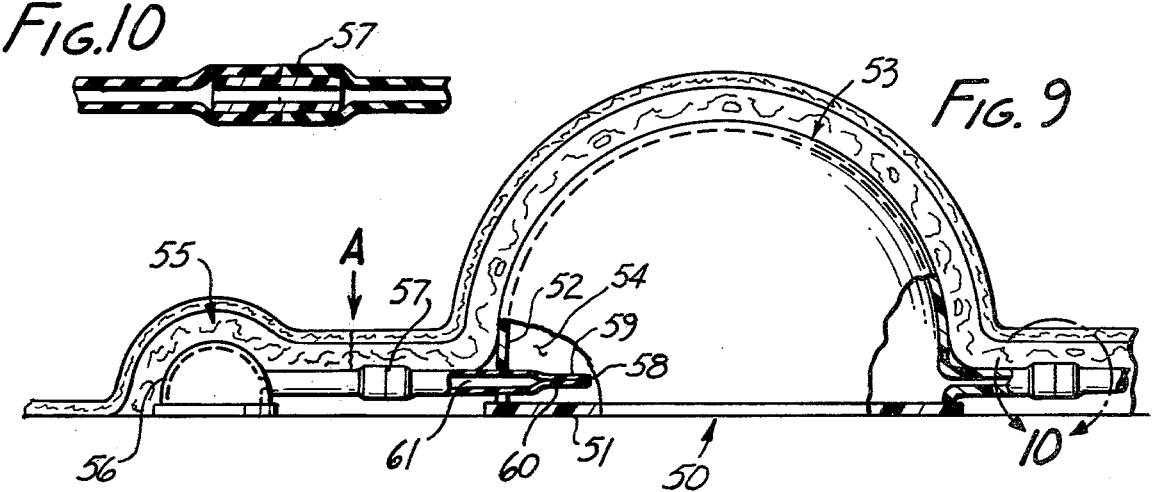
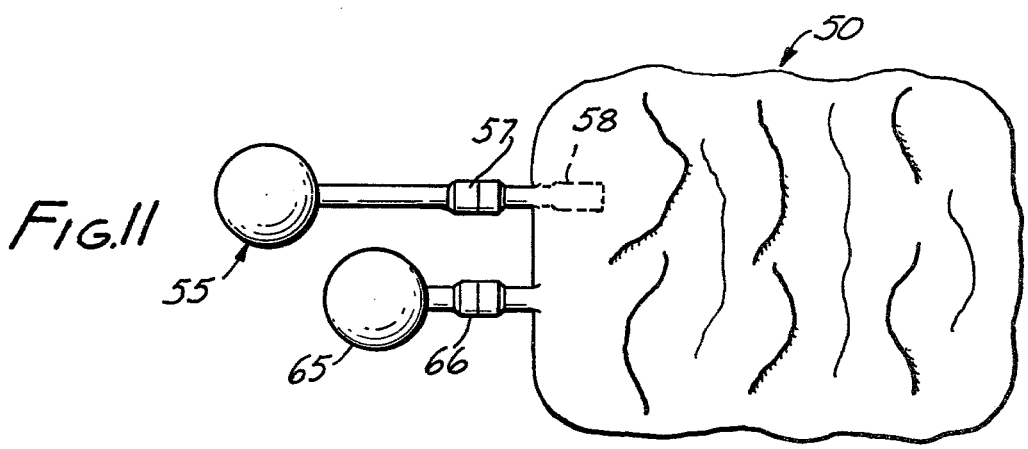
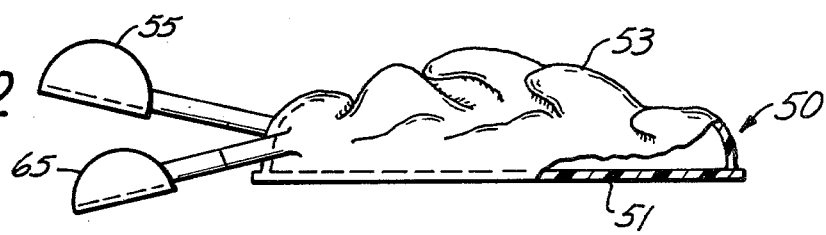
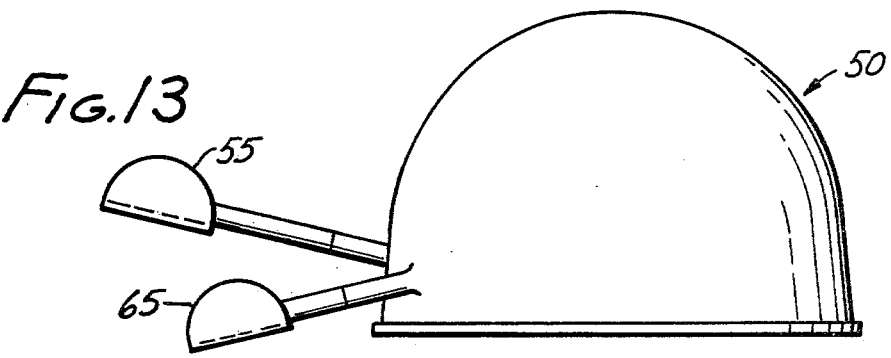

FLAP DEVELOPMENT DEVICE AND METHOD OF PROGRESSIVELY INCREASING SKIN AREA

This is a continuation of application Ser. No. 723,338 filed Sept. 15, 1976 now abandoned.

This application relates to the development of flap for usage in plastic and reconstructive surgery.

The art of plastic and reconstructive surgery is based on the successful use of free skin grafts, advancement of contiguous tissue, or pedicled flaps of various sizes and shapes. In the course of reconstruction of large defects, the ratio of tissue used for repair to the area repaired is on a one-to-one basis. Therefore, one area is repaired at the expense of another.

It is well known that skin and its subcutaneous tissue can greatly be expanded in area is the expansion is accomplished gradually. The extension of the skin over the pregnant female's abdomen is one example. As another example, African women have had their lower lips expanded to as much as twenty five inches in circumference. Further, huge benign tumors often exist in various parts of the body, and the skin and subcutaneous tissue covering these tumors is greatly enlarged, but still is normal in color and texture. This invention takes advantage of this function of the skin and subcutaneous tissue to generate a flap which can then be utilized in another area, usually, but not always, directly adjacent to the place where the expansion occurred. When it is directly adjacent, the skin areas will closely match after surgery, which is a profound improvement over much of the prior art.

The term "flap" is well known to surgeons. It is an area of skin with its underlaying subcutaneous tissue disconnected from the underlaying and surrounding tissue except at one edge. It is customary to apply the flap to a recipient area. It remains connected to adjacent tissue at its original situs until blood circulation is established at its new situs, after which it is cut loose from the originally adjacent tissue, and remains in place, fully sustained, in its new situs.

There has been at least one previous attempt made to expand skin and subcutaneous layer. This is described in the February 1957 issue of *Plastic and Reconstructive Surgery*, Volume 19, No. 1, pp. 124–130. A balloon was placed in the neck beneath the ear with a tube passing through the skin for reception of fluid for expansion. This balloon was flexible in all directions. It had unfortunate results and undesirable features. For one, it exerted substantial forces in all directions, especially downward, and because the balloon was fully flexible in all directions, could exert localized forces. Excessive localized force on underlaying muscle can cause atrophy, which is undesirable. Another disadvantage is the risk of bursting of a stretched-membrane balloon. Another is the high risk of infection caused by the tube that passes through the skin. Suffice it to say, the potential advantages of skin enlargement has not to this day been made practical, many years after it was first suggested.

This invention does make this technique practicable, and with it there becomes available to the surgeon and to the patient many significant advantages. One important advantage is that a large adjacent flap can be developed next to the area to be covered. Then the skin applied to the new area will match the neighboring skin, both as to color and texture. This is a tremendous cosmetic advantage.

Another advantage is that the patient can be ambulatory and out of the hospital for much of the time during which his flap is being developed. This device is intended to be fully implanted, and enlarges a localized area, which can be protected by guard means. When the flap is applied to its new area, especially when it is an adjacent flap, there is not the necessity for immobilizing the individual in various grotesque positions as required by the existing grafting techniques. The individual can be nearly free. Hospitalization can greatly be reduced.

Still another advantage is that the grafting technique is no longer on a one-to-one basis. The generation of an enlarged flap leaves the donor situs covered, with tissue developed as a flap for grafting.

Still other advantages are that this device greatly minimizes the risk of infection, because it is entirely implantable and reduces localized forces beneath the device.

It is an object of this invention to provide a device which can be made in many useful shapes, which does not exert excessive local forces against underlaying tissue, which can be completely implanted and inflated by injection through the skin without puncturing its cover to reduce the risk of infection, and which can, if desired, be provided with means for selective deflation to avoid necrosis caused by too-rapid expansion.

An expansion device according to this invention is adapted for complete implantation beneath the subcutaneous layer, there to be enlarged for the purpose of increasing the surface area of tissue which overlays it, thereby creating tissue for a new flap for repair and reconstruction. The device comprises a base and an overlaying cover. The base and the cover are joined to form a continuous fluid-tight envelope. The base is substantially non-extensible and the cover is flexible. When the envelope is empty the cover is slack, whereby the volume of the envelope is determinable as a function of the amount of fluid contained therein. Means is provided for admitting fluid to the envelope without puncturing the base or the cover. The outside surface of the device consists of material which is not deleterious to human tissue for the relatively short period of time in which is is expected to remain in place.

According to a preferred but optional feature of the invention, said means comprises a reservoir having a wall which is self-sealing to the track of a removed hollow needle, and which has an internal cavity bounded at least in part by said wall, and a conduit interconnecting the cavity and the inside of the envelope, whereby fluid can be injected into the reservoir through a needle that pierces the skin and the wall of the reservoir, and then flow through the conduit to enlarge the envelope.

According to yet another preferred but optional feature of the invention, a unidirectional check valve is disposed between the reservoir and the envelope to permit flow of fluid only from the reservoir to the envelope.

The above and other features of this invention will be fully understood from the following detailed description and the accompanying drawings, in which:

FIG. 9 is a cross-section showing another embodiment of the invention;

FIG. 10 shows a portion of FIG. 9;

FIG. 11 is a top view of the device of FIG. 9 before enlargement;

FIG. 12 is a side view of FIG. 11; and

FIG. 13 is a side view of the device of FIG. 9 in its most distended condition.

Figure 1:
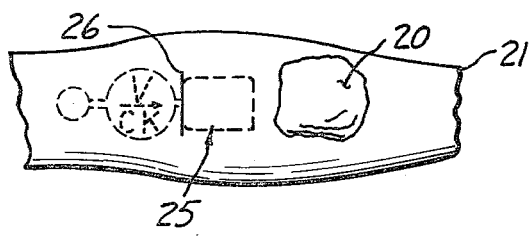
FIG. 1 is a schematic view of a person's arm with an implant according to the invention implanted beneath the skin and subcutaneous layer adjacent to a lesion.

FIG. 1 shows a lesion 20 on a human arm 21. A device 25 according to the invention is shown implanted beneath the skin and subcutaneous tissue. The implantation was made through an incision 26 which will have been closed by sutures. A pocket will have been formed by the surgeon beneath the subcutaneous layer in accordance with known surgical techniques, and the device is inserted in the pocket.

Figure 2:
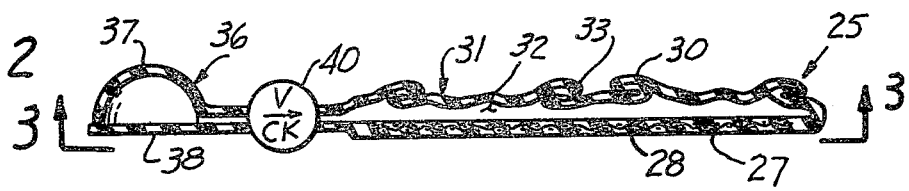
FIG. 2 is an axial cross-section of the presently preferred embodiment of the invention.
Figure 3:
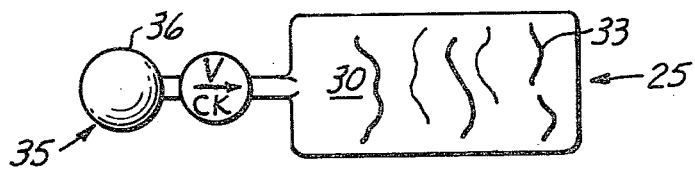
FIG. 3 is a bottom view taken at line 3—3 of FIG. 2.

The device 25 is best shown in FIGS. 2-7. It includes a base 27 which is substantially non-extensible. Preferably, it is either inflexible or stiffly flexible. Its limited extensibility, or lack of extensibility, causes its area-shape to be retained. Its stiffness (inflexibility or limited flexibility) prevents excessive localized forces from being exerte eneath the base, such as against underlying muscle. The stiffer the base is, the better is the distribution of force so as to avoid atrophy. The base may have embedded in it a relatively stiff fabric 28, or even a plate. The base may be made in any desired shape, thereby to determine the shape of the enlargement of the skin. It may be somewhat rectangular, as shown in FIG. 3. Often a somewhat elliptical shape will be preferred.

The base is overlaid by an overlaying cover 30 of flexible material. Although some stretching of this material is possible, the stretching of the material is intended to be avoided or minimized. This will limit the tendency of the material to thin out and perhaps spring a leak or burst. When the cover is joined to the base at its periphery, it forms a fluid tight envelope 31 with a chamber 32 therein. The cover is flexible, and when the envelope is empty, it is slack. The term "slack" means that there is sufficient material provided to enable the compartment to enlarge without stretching the material of the cover. It may, when slack, have random wrinkles 33 as shown or might even be formed with relatively concentric rings much like a bellows.

Because the device is intended to bear against underlying physiological structure, it is not possible to penetrate the base to inject liquid into the chamber. Because the envelope will be under substantial pressure, even though its material is not stretched, it is better not to perforate the cover for injection of fluid. Therefore, separate means 35 is provided for injecting liquid into the envelope. The liquid injected will usually be sterile saline solution or any other fluid which is compatible with human tissue should the device leak. The means comprises a reservoir 36 with a relatively thick, shape-retaining dome-shaped upper wall 37 and a base 38. The base 38 is flat and can lay directly against the tissue or bone beneath it. The reservoir is not intended to be flexible, though it may be slightly deformable. Its wall is intended to be self-sealing against needle tracks, and the reservoir is entirely implantable.

A unidirectional check valve 40 is connected between the reservoir and the chamber. It permits flow of liquid only into the chamber, and not the reverse. This check valve may conveniently have the same structure as check valve 58 (FIG. 9).

Figure 4:
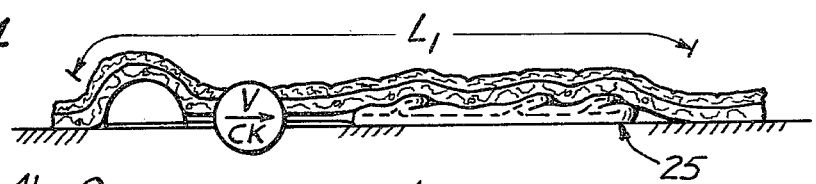
FIGS. 4, 5, 6 and 7 show the device of FIG. 2 implanted beneath the skin in progressive stages of enlargement.
Figure 5:
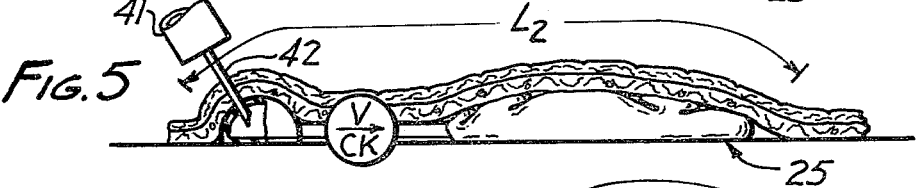
Figure 6:
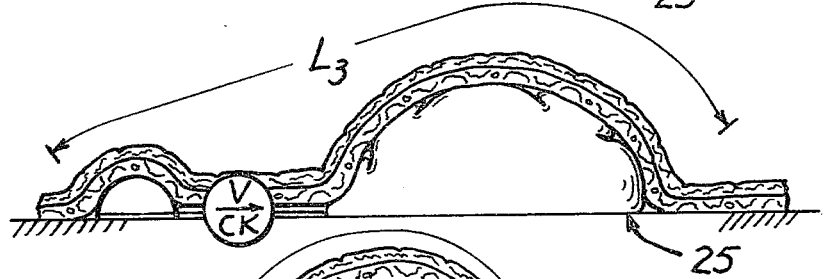
Figure 7:
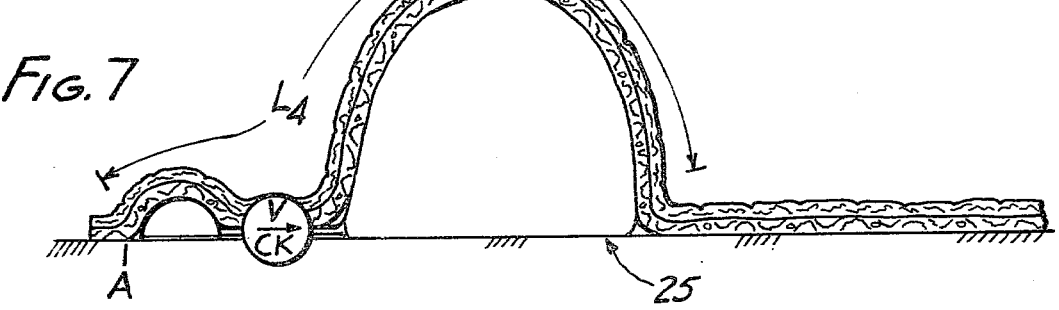
Figure 8:
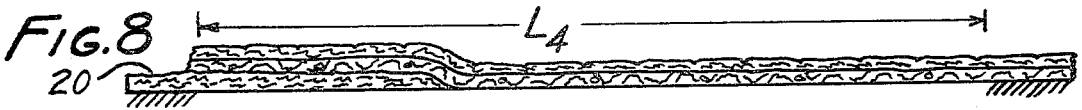
FIG. 8 shows the flap developed in FIG. 7 applied to a lesion.

The consequences of the foregoing are shown in FIGS. 4-7. In FIG. 4, the unfilled device 25 is shown implanted beneath the skin. A reference length L1 of overlaying skin is shown. A syringe 41 having a needle 42 pierces the overlaying tissue and the upper wall of the reservoir (as shown in FIG. 5) and injects liquid into the reservoir. The liquid is passed by the check valve and expands the envelope gradually, as shown in FIGS. 5, 6 and 7. This is done gradually over a period of time so that the skin and the subcutaneous layer expand to receive the larger volume placed beneath them. The gradually increasing reference lengths L2, L3, L4 (FIGS. 5, 6 and 7) show the extent of stretching the skin. The ultimate consequence is shown in FIG. 8 where the skin of the length L4 after removal of the device is shown stretched out to cover an adjacent lesion, such as lesion 20.

The area of the pocket does not appreciably increase when the device enlarges. The perimeter of the pocket appears to withstand "peeling" apart, so the skin enlargement is basically defined by the shape of the base. The pocket is formed by the surgeon just large enough to accommodate the base. When the area is substantial, the envelope when fully expanded will sometimes have a flat top, so that the cross-sections normal to the base are generally trapezoidal. This provides flatter flaps. However, convex flap skin is also useful, and larger areas can be developed with dome-like shapes as shown. Incidentally, it will be observed that the flap will be both longer and wider than the base, because the "length" of skin is increased in all directions.

It will be observed that in the device of FIG. 2 there is no means for reducing the size of the device in case an excessive amount of liquid has been added. Of course, the check valve can be omitted. Then liquid can be removed from the reservoir. Such an arrangement is within the scope of the invention. However, the check valve is very useful, because it isolates the means which is perforated by the needle from the envelope itself.

It is good practice to join the reservoir to the envelope by means of a connector, such as the connector shown in FIG. 10. Much of the risk of infection involved in the usage of this device arises at the site of injection, i.e., at and near the reservoir. Should infection occur, then an incision can be made, the reservoir disconnected at the connector and removed, and the incision closed until the infection has subsided. Thereafter, the reservoir can again be implanted. In the meanwhile, the skin and subcutaneous layer will have remained as enlarged as they already were, because the fluid is held in the chamber by the check valve.

The device of FIG. 9 provides a means for reducing the volume of the enlarged device. In device 50, a base 51 and a cover 52 are joined to form an envelope 53 with a chamber 54 having the same functions as those of the device of FIG. 2.

Similarly, a means 55 for admitting fluid to the envelope is provided which comprises a first reservoir 56 with the same properties as reservoir 36. The reservoir is connected to the envelope by a connector 57 (FIG. 10). A unidirectional check valve 58 having the same properties as check valve 40 is placed between them. This valve is a typical "bronx cheer" or miter-type valve having a pair of flat planar surfaces 59, 60 which are spread apart by a sufficient internal fluid pressure inside the conduit 61. It will be closed by reverse pressure against the outside of the blades. In the event that the volume of device 50 is to be reduced, a deflation reservoir 65 (sometimes called a "second reservoir") is provided. It has the same construction and features as first reservoir 56. It is moved to the opposite side of the device in FIG. 9 for convenience in illustration, but is shown correctly in FIGS. 11-13. Reservoir 65 is joined by connector 66 to the envelope. It has a stiff construction whose dome is penetrable by a needle, which is self-sealing to needle tracks, so that deflation can be accomplished by withdrawing fluid from reservoir 65 through a hollow needle, and then withdrawing the needle.

It is convenient for reservoirs 56 and 65 either to be differently sized or differently shaped so that they can be distinguished from one another by palpation when implanted beneath the skin.

The enlargement of the device of FIG. 9 is the same as that of FIG. 2. It has the additional feature of ready reduction in volume by removal of fluid from the device through the second reservoir.

This device is preferably entirely made of material which is compatible with human tissue for the period of time it is likely to be implanted. Basically, this is a temporary device, and its usage will be expected to be less than thirty days. Therefore, some materials may be used which are suitable for short-term implantation, but not for a longer term. However, well-known compatible materials, such as silicone rubber, which are suitable for long-term implantations, are much to be preferred. At least the exposed outer surfaces should consist of suitably compatible material, and the inside material can be incompatible.

The difference in extensibility between that of the base and of the cover can be provided by differences in thickness of the material, and/or by embedded reinforcement, as desired. The cover is preferably relatively thin, on the order of approximately 0.020 inch thick, while the base is relatively thicker and reinforced, preferably on the order of about 0.040 inch, with a polyester fabric reinforcement embedded therein.

The area of the base is selected for the intended usage. Successful implants as large as 6×9 inches and serving to develop as much as 54 square inches of flap have been made with a device having base dimensions of about 4×6 inches.

For implantation, a small incision is made, usually near the defect, although it may be made any other place desired. The surgeon forms the pocket with his fingers, and the device is inserted in the pocket. The incision is sutured closed. After the incision is sutured, a liquid, for example sterile normal saline, is injected into the implant by piercing the skin, subcutaneous layer, and reservoir with a hollow needle, usually 25 gauge, and injecting fluid into the reservoir through the check valve. The patient is able to maintain his full activity and need not be laid up in the hospital, as required by present surgical techniques.

Subsequent injections of additional liquid are performed in office procedures at an interval of about four to seven days. It is not uncommon for a flap of twice the area of the base to be developed in two weeks. In surgical procedures, another week is often allowed for adjustment and stabilization of the flap. Thereafter, the flap may be moved as desired in accordance with normal surgical techniques. There is no substantial difference in appearance of the normal and of the expanded skin, provided that the expansion has occurred gradually.

Reconstruction of the breast after modified radical mastectomy has been successfully accomplished with the development of a new breast utilizing 400 cc of normal saline injected into the envelope over a period of 2½ weeks. After initial injection of 150 cc at the time of implant insertion, gradual expansion was accomplished by injections of 40 to 60 cc of normal saline every three to six days.

The skin was successfully expanded and adjacent flap developed near open infected wounds of chronic osteomyelitis, injuries, burns, decubitus ulcers, or following malignant lesion radical surgery.

It will be seen that this device, and the method is enables to be used, have distinct advantages for the patient. They enable the patient to have a more perfect repair by gaining extra tissue of the same matching color and texture. It also eliminates much of the hospitalization time and expense usually utilized in conventional procedure. For the surgeon, it permits easier repair with better results and reduces the time spent in patient observation and follow-up.

This device can be utilized in the development of adjacent flaps anywhere on the body. It has the important feature that during usage it is entirely beneath the skin where it will not be harmed by contact with other bodies.

The reservoirs are not intended to be appreciably enlarged by the pressures involved. They are shape- and size-retaining. The expansion is confined to the envelope.

An additional reason why it is undesirable to perforate the cover to enlarge the device is that it would require the needle to perforate the stretched skin over it. Healing of the puncture at this place is less reliable.

It is possible that the skin and subcutaneous layer may occasionally be thinned down excessively by too-rapid enlargement. Then the blood supply to localized areas of the skin over the cover may be insufficient, and localized necrosis might occur. Deflation means enables the tension to be relieved quickly and easily by withdrawing a small amount of fluid from the device. It is an advantage to be able to withdraw the fluid at a region spaced from the envelope which is not already in trouble.

This invention is not to be limited by the embodiments shown in the drawings and described in the description, which are given by way of example and not of limitations, but only in accordance with the scope of the appended claims.

We claim:

1. An expansion device having variable external sides for complete implantation beneath the skin and subcutaneous layer, there to be enlarged, whereby to increase the surface area of skin and subcutaneous layer which overlay it, said device comprising: a base, an overlaying cover, said base and cover being joined to form a continuous fluid-tight envelope with a chamber therein, the base being substantially non-extensible, the cover being flexible, and when the envelope is empty, is slack, whereby the volume of the envelope is determinable as a function of the amount of fluid contained in the chamber; means outside the envelope for admitting fluid to the chamber without puncturing the base or the cover, the outside surface of said device consisting of material which is compatible with human tissue for the period of time it is intended to be implanted therein; a unidirectional check valve disposed in the path of fluid flow from said means to said chamber; a deflation reservoir which has a wall that is self-sealing to the track of a hollow needle, and which forms an internal cavity bounded at least in part by said wall; and a conduit interconnecting said cavity and the chamber, whereby fluid can be withdrawn from the chamber through a needle piercing the skin, the subcutaneous layer and the wall of said deflation reservoir.

2. A device according to claim 1, in which the base is stiffly flexible.

3. A device according to claim 1, in which the base is rigid.

4. A device according to claim 1, in which said reservoir is connected to the envelope by a disconnectible connector, whereby said reservoir can be separated from said envelope.

5. An expansion device having variable external sides for complete implantation beneath the skin and subcutaneous layer, there to be enlarged, whereby to increase the surface area of skin and subcutaneous layer which overlay it, said device comprising: a base, an overlaying cover, said base and cover being joined to form a continuous fluid-tight envelope with a chamber therein, the base being substantially non-extensible, the cover being flexible and when the envelope is empty, is slack, whereby the volume of the envelope is determinable as a function of the amount of fluid contained in the chamber; a reservoir outside the envelope for admitting fluid to the chamber without puncturing the base or the cover, said reservoir having a wall which is self-sealing to the track of a hollow needle, and having an internal cavity bounded at least in part by said wall, and a conduit interconnecting said cavity and the chamber, whereby fluid can be injected into the reservoir through a needle piercing the skin, subcutaneous layer, and the wall, and flow into the chamber; a unidirectional check valve disposed in the path of fluid flow from the cavity to the chamber, permitting flow only in that direction; a second reservoir which has a wall that is self-sealing to the track of a hollow needle, and which forms an internal cavity bounded at least in part by said wall, and a conduit interconnecting said cavity and the chamber, whereby fluid can be withdrawn from the chamber through a needle piercing the skin, subcutaneous layer and the wall of said second reservoir; and the outside surface of said device consisting of a material which is compatible to human tissue for the period of time it is intended to be implanted therein.

6. A device according to claim 5, in which the base is stiffly flexible.

7. A device according to claim 5, in which the base is rigid.

8. A device according to claim 5, in which the said reservoirs are connected to the envelope by disconnectible connectors, whereby said reservoirs can be separated from said envelope.

9. An expansion device having variable external size for complete implantation beneath the skin and subcutaneous layer, there to be enlarged, whereby to progressively increase the surface area of skin and subcutaneous layer which overlay it over a prolonged period of time after implantation, said device comprising: a base, an overlaying cover, said base and cover being joined to form a continuous fluid-tight highly expandable envelope with a chamber therein, the base being substantially non-extensible, and substantially stiffer than the cover for controlling the envelope shape during progressive size increases over a prolonged period of time, the cover being flexible, and when the envelope is empty, is slack with the envelope collapsible to substantially less than one half of its inflatable volume for insertion under a section of skin, whereby the volume of the envelope is determinable as a function of the amount of fluid contained in the chamber; and a substantially less expandable puncture chamber in flow communication with the envelope and located outside the envelope for admitting fluid to the chamber by periodic hypodermic injections through the skin and subcutaneous layer without puncturing the base or the cover, the outside surface of said device consisting of material which is compatible with human tissue for the period of time it is intended to be implanted therein.

10. A device according to claim 9, in which a unidirectional check valve is disposed in the path of fluid flow from said puncture chamber to said envelope chamber.

11. A device according to claim 10, in which the base is stiffly flexible.

12. A device according to claim 10, in which the base is rigid.

13. A device according to claim 9, in which said puncture chamber comprises a reservoir having a wall which is self-sealing to the track of a hollow needle, and having an internal cavity bounded at least in part by said wall, and a conduit interconnecting said puncture chamber and the envelope chamber, whereby fluid can be injected into the puncture chamber through a needle piercing the skin subcutaneous layer, and the wall, and flow into the envelope chamber.

14. A device according to claim 13, in which a unidirectional check valve is disposed in the path of fluid flow from the puncture chamber to the envelope chamber, permitting flow only in that direction.

15. A device according to claim 13, in which the said puncture chamber is connected to the envelope by a disconnectible connector, whereby said puncture chamber can be separated from said envelope.

16. A device according to claim 9, in which the base is stiffly flexible.

17. A device according to claim 9, in which the base is rigid.

18. A device according to claim 9, in which said puncture chamber is connected to the envelope by a disconnectible connector, whereby said puncture chamber can be separated from said envelope.

19. A device according to claim 18, in which a check valve is disposed in the path of fluid flow between the connector and the envelope.

20. A device according to claim 19, in which said check valve is disposed inside said envelope.

21. The method of progressively enlarging over a prolonged period of time the area of skin and subcutaneous layer overlaying a reference area, comprising: making an incision through the skin and the subcutaneous layer; forming a pocket about the size and shape of the reference area; implanting in said pocket a device having variable external size and having a substantially non-extensible base substantially the size and shape of the reference area, said device having a slack, flexible cover joined to and overlaying the base to form a fluid-tight envelope, the cover laying contiguous to the subcutaneous layer; and further implanting means beneath the skin which is fluidly interconnecting with said envelope to receive fluid and pass said fluid to the envelope; closing the incision; and then periodically injecting fluid through the skin and subcutaneous layer into said means to externally enlarge the envelope.

22. The method of claim 21, in which the said injection is made by the use of a syringe and a hollow needle, the needle penetrating the skin, the subcutaneous layer, and the said means.

23. A device to progressively increase skin area over a prolonged period of time after surgical implantation, comprising: a highly expandable skin stretching chamber joined in flow communication with a substantially less expandable puncture chamber; said skin stretching chamber having a shape retaining base that is substantially stiffer than a flexible cover of the skin stretching chamber for controlling the shape of such skin stretching chamber during progressive enlargement; and the skin stretching chamber is collapsible to a volume substantially less than one half of its inflatable volume for insertion under a section of skin, whereby the skin stretching chamber can be progressively enlarged by periodic hypodermic injections through the skin into the puncture chamber.

24. A device as set forth in claim 23, wherein the puncture chamber is substantially nonexpandable.

25. A device as set forth in claim 23, wherein the two chambers are joined by a tube smaller than either chamber.

26. A device as set forth in claim 23, wherein the puncture chamber is of a material that reseals itself after withdrawal of a hypodermic needle.

27. A device as set forth in claim 23, wherein the puncture chamber has a generally dome shaped upper portion for puncture and a generally flat bottom portion.

28. A device as set forth in claim 23, wherein there is a one-way check valve between the two chambers.

29. A device as set forth in claim 23, wherein the skin stretching chamber has spaced apart inlet and outlet openings, the inlet opening connected to a conduit for injecting fluid into the chamber, and the outlet opening connected to a conduit for removing fluid from the chamber.

30. A method of progressively increasing skin area over a prolonged period of time, comprising the steps of:
(a) placing beneath the skin a device that includes a highly expandable skin stretching chamber joined in flow communication to a substantially less expandable puncture chamber, said skin stretching chamber having a base that is substantially stiffer than a flexible cover of the skin stretching chamber, and such skin stretching chamber is collapsible to a volume substantially less than one half of its inflatable volume for insertion under a section of skin; and
(b) progressively enlarging the skin stretching chamber by periodic hypodermic injections through the skin into the puncture chamber.

31. A method as set forth in claim 30, wherein the method also includes surgically removing the device after the skin has been progressively stretched over the prolonged period of time to its desired area.

* * * * *